United States Patent [19]

Smith, III

[11] Patent Number: 5,514,148
[45] Date of Patent: May 7, 1996

[54] SURGICAL CLAMP AND METHOD OF USE

[76] Inventor: Ray C. Smith, III, 12445 Silver Bay Cir., Indianapolis, Ind. 46236

[21] Appl. No.: 334,413

[22] Filed: Nov. 4, 1994

[51] Int. Cl.$^6$ .................................................. A61B 17/04
[52] U.S. Cl. .......................... 606/151; 606/206; 606/207
[58] Field of Search ................................... 606/151, 108, 606/205–208, 142; 604/174

[56] References Cited

U.S. PATENT DOCUMENTS

| | | | |
|---|---|---|---|
| 3,404,677 | 10/1968 | Springer | 606/206 |
| 3,782,381 | 1/1974 | Winnie . | |
| 4,484,911 | 11/1984 | Berlin et al. | 128/214.4 |
| 4,792,330 | 12/1988 | Lazarus et al. | 604/174 |
| 4,815,476 | 3/1989 | Clossick | 606/208 |
| 4,817,604 | 4/1989 | Smith, III | 606/151 |
| 4,904,246 | 2/1990 | Atkinson | 604/264 |
| 4,935,017 | 6/1990 | Sylvanowicz | 604/280 |
| 5,149,327 | 9/1992 | Oshiyama | 604/167 |
| 5,183,470 | 2/1993 | Wettermann | 604/281 |
| 5,221,253 | 6/1993 | Coll | 604/8 |
| 5,250,056 | 10/1993 | Hasson | 606/208 |
| 5,281,230 | 1/1994 | Heidmueller | 606/207 |
| 5,304,187 | 4/1994 | Green et al. | 606/151 |
| 5,354,312 | 10/1994 | Brinkerhoff et al. | 606/207 |

*Primary Examiner*—Gary Jackson
*Attorney, Agent, or Firm*—Woodard, Emhardt, Naughton, Moriarty & McNett

[57] ABSTRACT

A surgical clamp and method of use of same. The surgical clamp has (a) a shaft with proximal and distal ends; (b) two opposing jaw members with proximal ends, distal ends, cooperating faces, and lateral faces, the jaw members hingedly attached at their proximal ends to the distal end of the shaft, the jaw members adapted to clamp tissue placed between the cooperating faces; (c) a cylinder slidably disposed around the shaft, the cylinder adapted to urge the opposing jaws together when is axially displaced toward the distal end of the shaft and over the lateral faces of the jaw members; and (d) the shaft the jaw members and the cylinder is formed of radiolucent material.

7 Claims, 8 Drawing Sheets

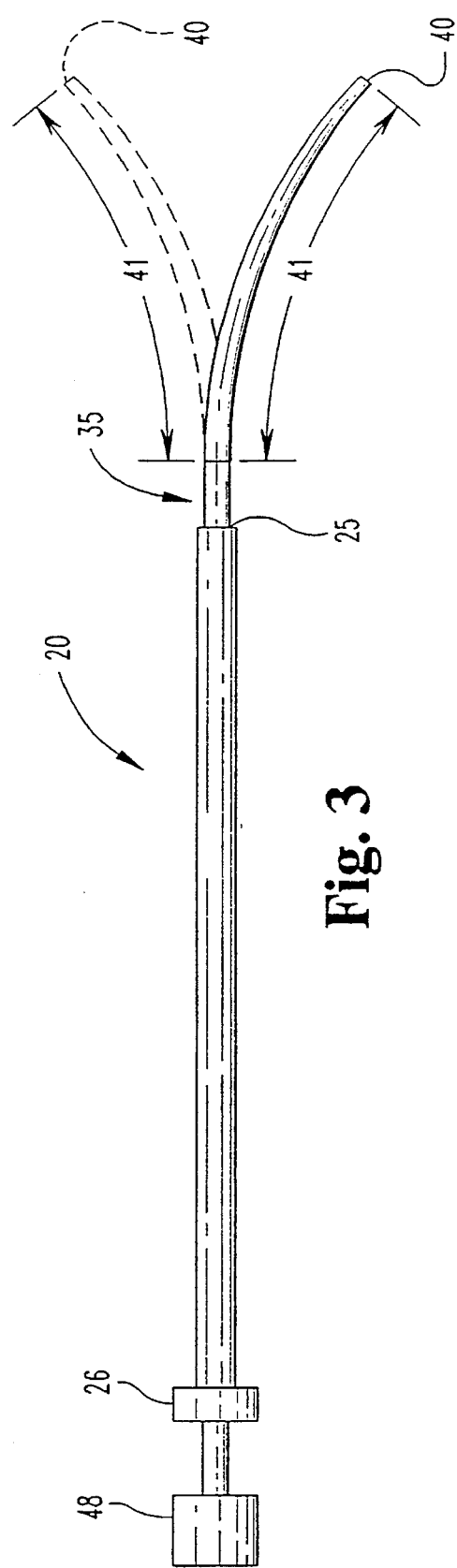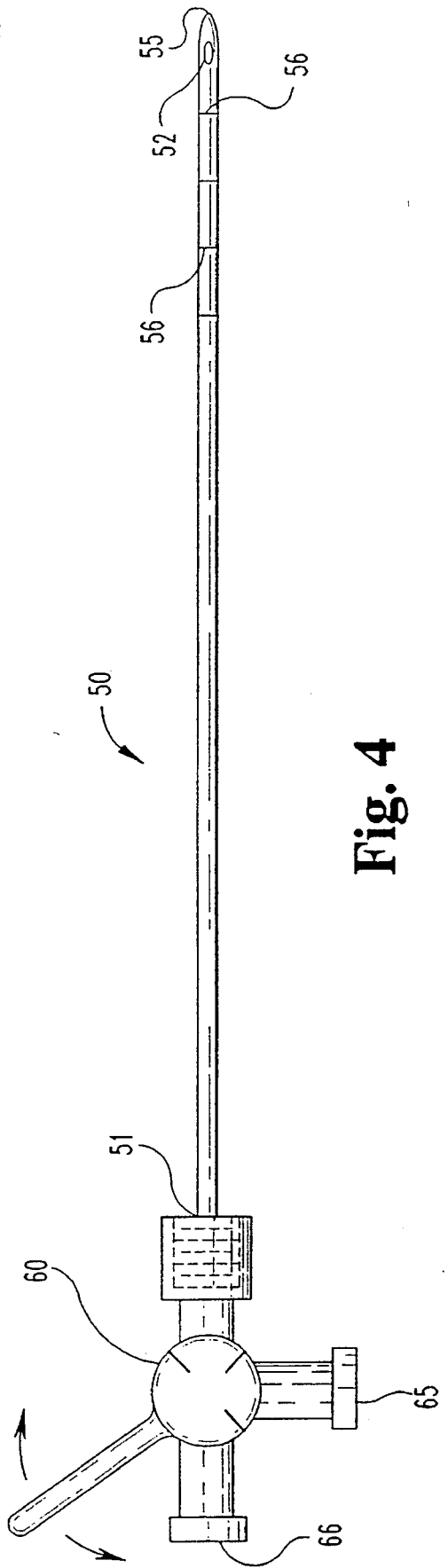
Fig. 3
Fig. 4

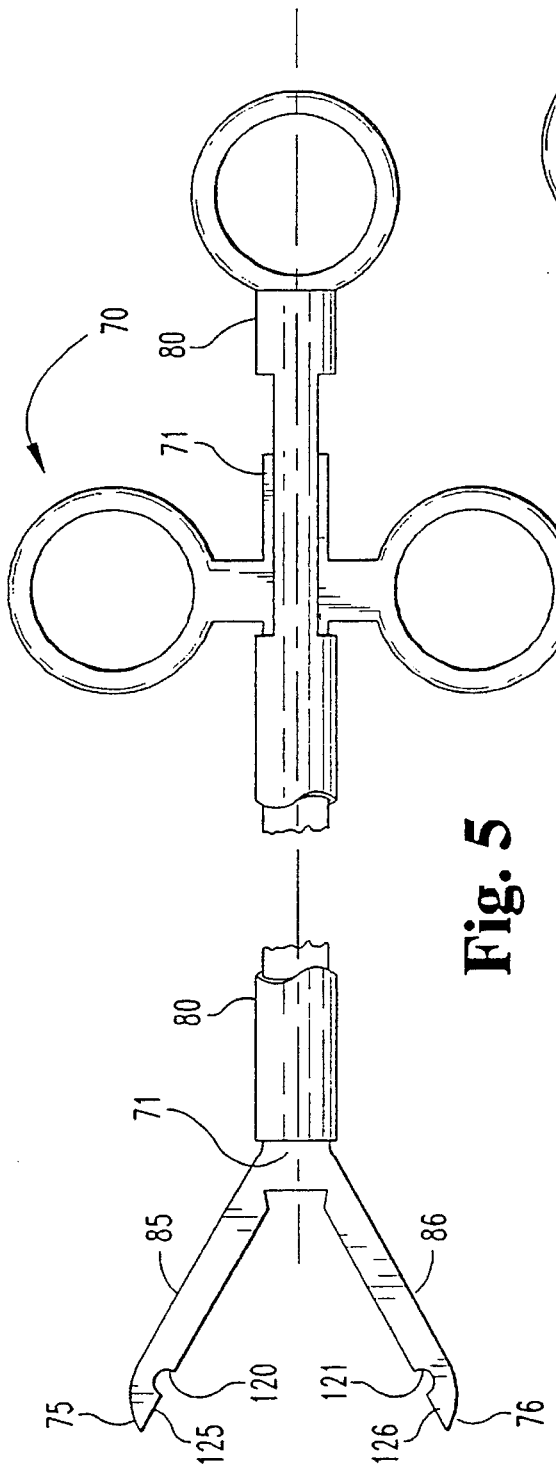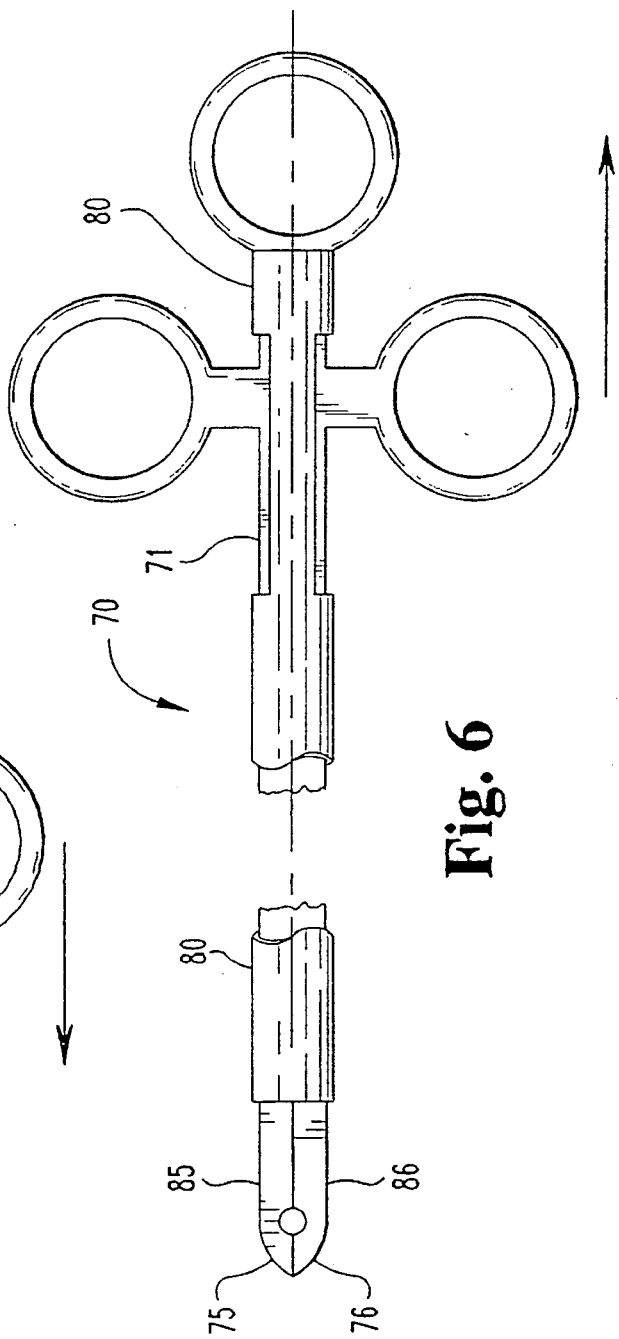

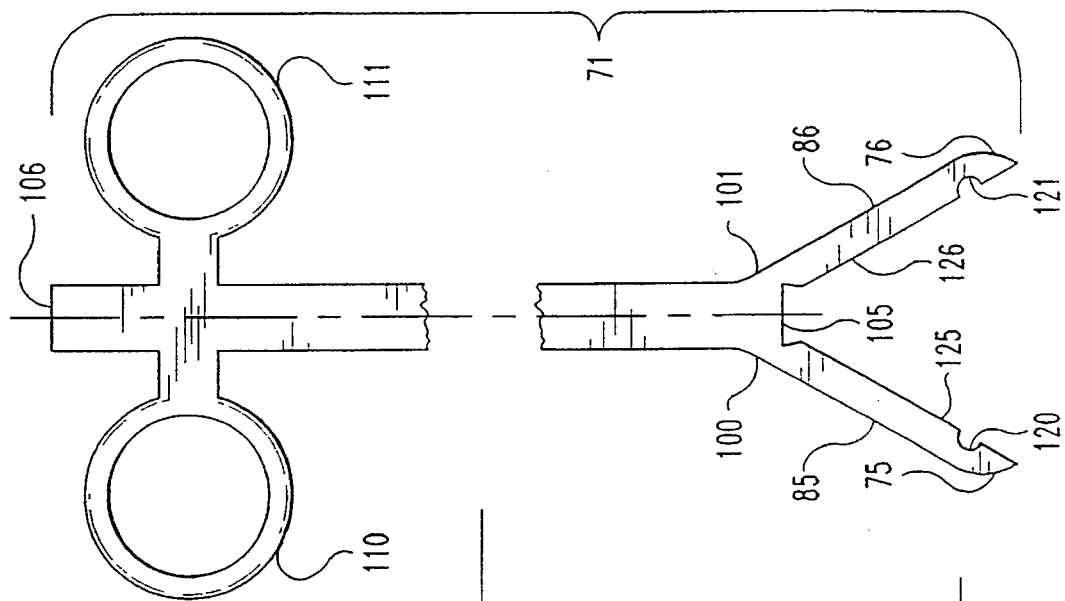
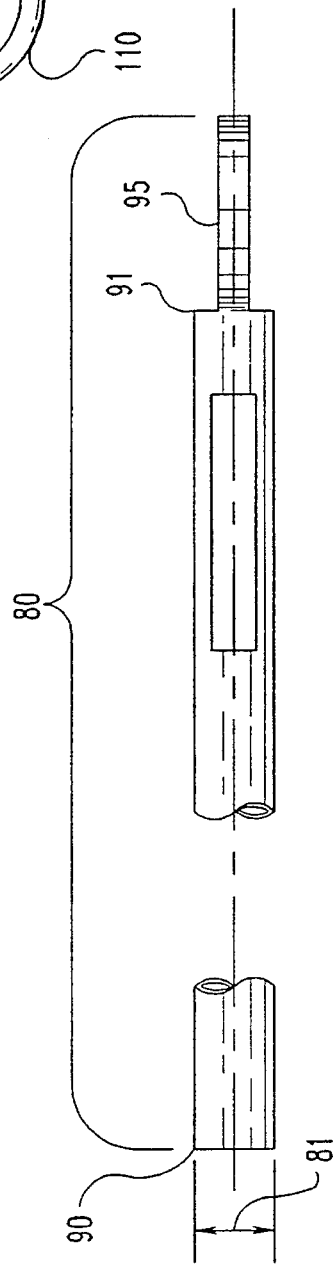
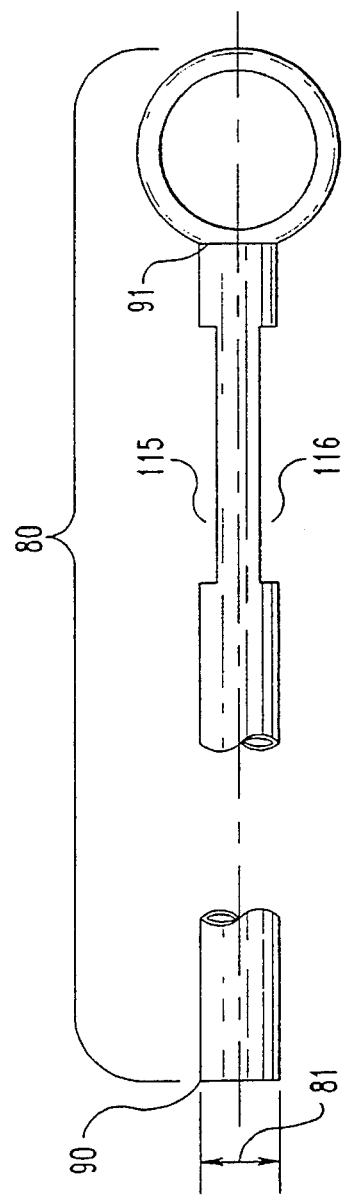

SURGICAL CLAMP AND METHOD OF USE

CROSS REFERENCE TO RELATED APPLICATION

This application is based on my abandoned U.S. patent application Ser. No. 08/109,663, filed Aug. 20, 1993 now abandoned.

BACKGROUND OF THE INVENTION

This invention generally pertains to surgical instruments, and more particularly to catheters and surgical tissue clamps.

A typical cannula smoothly introduces a long catheter into a body cavity. The cannula is initially placed within the body and then the catheter is pushed through the cannula. The catheter is extended past the distal end of the cannula and guided further into the body to the desired location. An example of such a location is the cystic duct residing just below the gall-bladder.

Guiding a flexible catheter within the body can be a time-consuming and frustrating procedure. A wire guide has been used inside the catheter to guide the catheter into position. Such guides are useful for deep penetrations into the body; however, their use may be inefficient in comparatively shallow surgeries. Comparatively shallow surgeries allow the catheter to be positioned without the additional time required to use a wire guide. Although, without the guide, sinuously routing a flexible catheter into place may increase frustration while simultaneously shortening the time required for the surgery.

What is needed is a method and device to cannularize and further guide a catheter into position without using a device that routinely requires removal during surgery. Such a device would shorten the time required to use a catheter by avoiding time necessary to use and remove an internal wire guide.

Other problems associated with catheterizations include the radiopaque nature of most surgical tools. Should X-rays be involved in the operation, often surgical tools block critical areas of tissue from view. Accordingly, what is also needed is a device that guides the catheter into place which is also radiolucent.

Associated to the aforesaid obstruction problem are clamps used in conjunction with particular catheterizations. In conventional procedures, the clamps may obstruct the view in a radiograph.

U.S. Pat. No. 4,817,604 discloses a partially radiolucent clamp for use with catheters. The clamp is routinely used in transcystic duct operative cholangiography and the spring within this clamp is visible in the radiograph. The clamp consists of a pair of jaws that are positioned into place with needle nose shaped clips. The clamp works fine; however, the two-piece design requires assembly by the user before its use.

What is needed is a clamp that is easily attached and removed. The clamp must be entirely radiolucent so that no radiopaque parts need to be removed to allow roentgenographic examination.

SUMMARY OF THE INVENTION

Briefly describing one aspect of the present invention there is provided a surgical clamp and method of use of same. The surgical clamp comprises (a) a shaft with proximal and distal ends; (b) two opposing jaw members with proximal ends, distal ends, cooperating faces, and lateral faces, the jaw members hingedly attached at their proximal ends to the distal end of the shaft, the jaw members adapted to clamp tissue placed between the cooperating faces; (c) a cylinder slidably disposed around the shaft, the cylinder adapted to urge the opposing jaws together when the cylinder is axially displaced toward the distal end of the shaft and over the lateral faces of the jaw members; and (d) the shaft, the jaw members, and the cylinder formed of radiolucent material.

BRIEF DESCRIPTION OF THE DRAWINGS

In the accompanying drawings, forming a part of this specification, and in which like numerals are employed to designate like parts throughout the same, FIG. 3 is a front view of cannula-guide assembly according to one embodiment of the present invention, FIG. 4 is a front view of a catheter according to one embodiment of the present invention, FIGS. 5 and 6 are fragmented front views of a surgical clamp according to one embodiment of the present invention, FIGS. 7 and 8 are respectively fragmented side and front views of a cylinder according to one embodiment of the present invention, FIG. 9 is a fragmented front view of a shaft according to one embodiment of the present invention.

DESCRIPTION OF THE PREFERRED EMBODIMENTS

Figure 1:
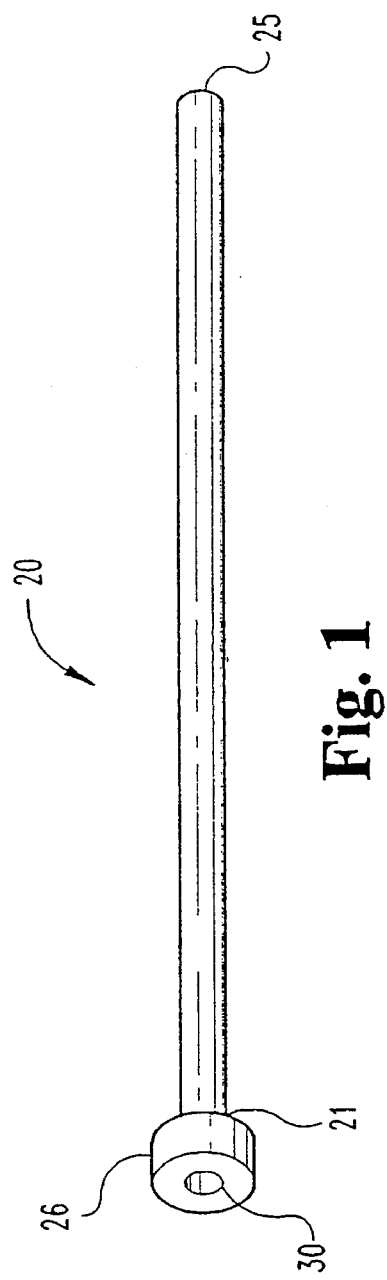
FIG. 1 is a front view of a cannula according to one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As stated, the present invention relates to a catheter assembly and surgical clamp. The catheter assembly includes a cannula, a guide, and a catheter. The clamp includes two opposing jaw members attached to the distal end of a shaft and is formed of radiolucent material. The present description begins with the catheter assembly.

Referring to FIG. 1, there is shown cannula 20 in accordance with one embodiment of the present invention. Cannula 20 comprises a hollow tube. The cavity within cannula 20 opens at both its proximal end 21 and its distal end 25.

Cannula 20 can be of any length or diameter appropriate to perform a particular surgery. A particularly useful length is about 15 to about 30 centimeters, or preferably is about 20 centimeters. A common range of usable inside diameters is about 3 to about 15 millimeters, or preferably is about 5 millimeters.

Cannula 20 is formed of any compatible material for insertion within the body including many metals and plastics. A radiolucent material is particularly preferable and includes most plastics. Radiolucent material is preferable because roentgenographic examination is often used to monitor or to conduct surgery with catheters. Radiolucent material allows the surgeon to view tissue residing in line with the cannula and the X-ray source. This tissue would otherwise be obstructed from the surgeons view by the cannula.

In the embodiment of cannula 20 shown in FIG. 1, there is guide seal 26 attached to proximal end 21. Guide seal 26 is useful to prevent gas from flowing into the cannula. Guide seal 26 has a guide aperture 30 disposed through the seal permitting the passage of at least one guide or catheter. The aperture may have a cross section that is round, oblong, or simply a slit. When a guide is inserted in cannula 20, the opening between the guide and the cannula is sealed by the sidewalls of the aperture pressing against the sides of the guide. Guide seal 26 is formed of any elastic material suitable for use during surgery including plastic, rubber, natural rubber, and sponge.

Figure 2:
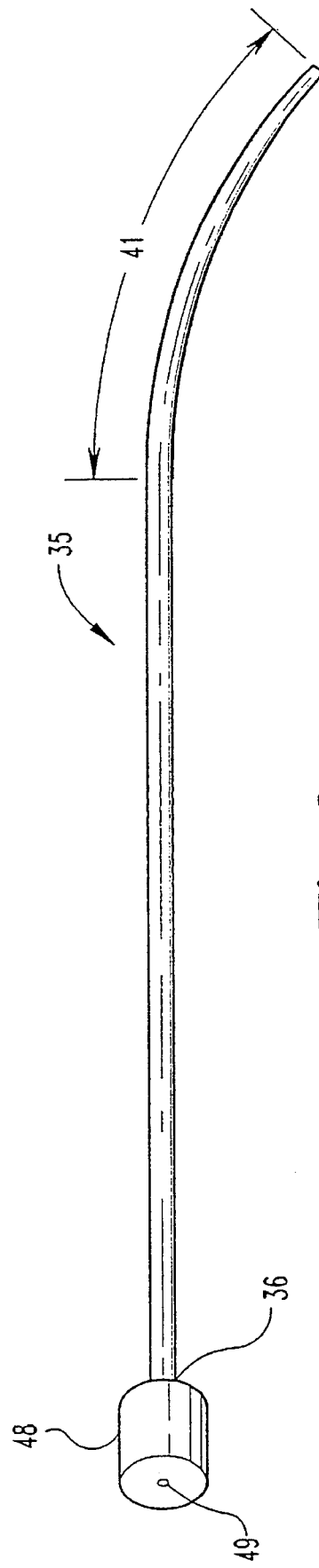
FIG. 2 is a front view of a guide according to one embodiment of the present invention.

Referring to FIG. 2, there is shown guide 35 in accordance with one embodiment of the present invention. Guide 35 has a tubular structure and is formed of rigid material. Similarly to cannula 20, the cavity within guide 35 opens at both its proximal end 36 and its distal end 40. Guide 35 has an outside diameter appropriate to slidably engage and reside within cannula 20 (See FIG. 3.) which allows guide 35 to slide and rotate within cannula 20.

Guide 35 is formed of any compatible material for insertion within the body which is radiolucent. This includes most plastics. As previously mentioned regarding cannula 20, radiolucent material is preferable because roentgenographic examination is often used to monitor or to conduct surgery with catheters. Radiolucent material allows the surgeon to view tissue residing in line with the guide and the X-ray source. This tissue would otherwise be obstructed from the surgeons view by the guide.

A characteristic of guide 35 is curved shape 41 near distal end 40. Curved shape 41 is permanently shaped within guide 35 and is capable of resiliently deforming if forced straight. This occurs when guide 35 is placed in a retracted position within cannula 20, meaning, to pull distal end 40 toward or completely inside cannula 20. This retracted position forces curved shape 41 to straighten. Then, when distal end 40 of guide 35 is pushed forward and extruded past distal end 25 of cannula 20; curved shape 41 returns and thereby moves distal end 40 laterally away from cannula 20. This movement allows the surgeon to place the distal end 40 to a desired location within the body by rotating guide 35 within cannula 20 and varying the extension of guide 35 past distal end 25.

In the embodiment of guide 35 shown in FIGS. 2 and 3, there is catheter seal 48 attached to proximal end 36 of guide 35. Catheter seal 48 is useful to prevent gas from flowing into the guide. Catheter seal 48 has a catheter aperture 49 disposed through the seal permitting the passage of at least one catheter. The aperture may have a cross section that is round, oblong, or simply a slit. When a catheter is inserted into guide 35, the opening between the catheter and the guide is sealed by the sidewalls of the aperture pressing against the sides of the catheter. Catheter seal 48 is formed of any elastic material suitable for use during surgery including plastic, rubber, natural rubber, and sponge.

Referring now to FIG. 4, there is shown catheter 50 according to one embodiment of the present invention. Catheter 50 may be of any length and diameter suitable to perform a particular surgery. Examples of usable lengths include about 50 to about 65 centimeters. The cavity within catheter 50 opens at its proximal end 51 into stopcock 60 and at catheter exit 52 near its distal end 55. The catheter exit can be located in any suitable position at or near its distal end and an example of a usable location is 3 millimeters from distal end 55. The catheter can be constructed of any material suitable for use as a catheter provided the resulting catheter has enough flexibility to slidably engage the length of guide 35.

A preferable feature of catheter 50 is the placement of longitudinal grooves 56 evenly spaced over the length of catheter 50 near distal end 55. Grooves 56 are preferably ascertainable under roentgenographic examination when the catheter is in the body. Grooves 56 assist the surgeon to judge the penetration depth of distal end 55 past or into a particular area.

In the embodiment of catheter 50 shown in FIG. 4, there is 3-way stopcock 60 mechanically attached to proximal end 51 of catheter 50. A stopcock is a valve for regulating the flow of a liquid. Stopcock 60 has two fluid ports 65 and 66 through which two fluid sources can be selectively controlled through catheter 50. An example of their use would be that a surgeon could use one port to inject saline into body tissue for irrigation, and with a turn of the stopcock, the surgeon could use the second to introduce radiopaque dye into the tissue. The use of a stopcock prevents the surgeon from having to mechanically connect and disconnect various fluid sources.

The preferred embodiment of the catheter assembly described supra is contemplated to be used in the following manner. The three-piece assembly is preassembled before insertion into the patient. Catheter 50 is slidably engaged into guide 35 but is not allowed to extend past distal end 40. These two pieces are then, as a unit, slidably engaged into cannula 20.

The three piece assembly is inserted into the patient. The assembly including cannula 20, guide 35 slidably engaged and residing within cannula 20, and catheter 50 slidably engaged and residing within guide 35; catheter 50 and guide 35 being fully retracted within cannula 20 as cannula 20 is first placed into position. Guide 35 is then rotated and extended further into the patient so that the curvedly shaped portion of guide 35 extends distal end 40 distally and laterally from cannula 20. Distal end 40 of guide 35 is then located immediately adjacent the particular canal, vessel, duct, or body cavity of interest. Catheter 50 .is then pushed into the canal, vessel, duct, or body cavity. If this particular surgery is performed with the aid of an X-ray device, the guide will not block the surgeons view as it is formed of radiolucent material. A particular example involving gallbladder surgery is discussed infra.

Referring now to FIGS. 5 and 6 there is shown a surgical clamp 70 in accordance with one embodiment of the present invention. Clamp 70 includes shaft 71, opposing jaw members 75 and 76, and cylinder 80.

FIG. 5 depicts this embodiment of the invention with opposing jaw members 75 and 76 in the open position. Jaw members 75 and 76 are in the open position because shaft 71 is axially displaced from cylinder 80 in a direction that is distal to the user.

FIG. 6 depicts this embodiment of the invention with opposing jaw members 75 and 76 in the closed position. Jaw members 75 and 76 are forced closed by forcing internal diameter 81 (FIG. 7 or FIG. 8) of cylinder 80 over lateral faces 85 and 86, respectively of jaw members 75 and 76. Internal diameter 81 is forced over lateral faces 85 and 86 when shaft 75 is axially displaced into cylinder 80 in a direction that is proximal to the user.

FIGS. 7 and 8 show an isolated embodiment of cylinder 80. Cylinder 80 is hollow having its internal cavity opening at distal end 90. Internal diameter 81 must be of a dimension to slidably engage shaft 71 while also being of a dimension able to urge jaw members 75 and 76 closed.

At proximal end 91 of cylinder 80 is preferably a thumb positioner. Thumb positioner 95 can be of any design suitable or adapted to convey force of the human thumb onto cylinder 80 in order to axially displace cylinder 80 in respect to shaft 71. Thumb positioner 80 is also helpful to locate the human thumb in the proper location to use the surgical clamp.

FIG. 9 shows an isolated view of shaft 71. The cross sectional configuration of shaft 71 must be that allowing the shaft to slidably engage cylinder 80 and allowing cylinder 80 to slide over lateral faces 85 and 86 of jaw members 75 and 76. Jaw members 75 and 76 are respectively attached at their proximal ends 100 and 101 to distal end 105 of shaft 71. This attachment can occur with any means that allows the jaws to open and close; although, a preferable embodiment includes the living hinge shown in FIG. 9. A living hinge is formed by narrowing the width of material used to attach jaw members 75 and 76 to shaft member 71. The narrow width becomes the locus of bending when a jaw member is moved relative to shaft member 71. A preferable means to construct a living hinge is by simultaneously molding jaw members 75 and 76 and shaft member 71 with relatively more narrow material forming the attachment between the jaw members and the shaft. Preferably the hinges are molded in the open position so that they have a tendency to stay open when no force is exerted to close them.

Near proximal end 106 of shaft 71 is at least one, but preferably two, finger positioners 110 and 111. If two finger positioners are used it is preferable that they be diametrically attached to each side of shaft 71. Finger positioners 110 and 111 extend through slots 115 and 116 in cylinder 80 (FIG. 8) when the surgical clamp is assembled. These positioners are designed and adapted to convey force from a finger to axially displace shaft 71 relative to cylinder 80 and they are also helpful to readily locate the human fingers in the proper place to use the surgical clamp.

A preferable means to assemble surgical clamp 70 requires finger positioners 110 and 111 to be attached last. Proximal end 106 of shaft member 71, without finger positioners 110 and 111, is first inserted into cylinder 80. Finger positioners 110 and 111 are then attached once proximal end 106 slides past longitudinal slots 115 and 116. Shaft member 71 will not slide completely back out from cylinder 80 with finger positioners 110 and 111 attached because shaft member 71's axial movement is now limited by the length of longitudinal slots 115 and 116.

Surgical clamp 70 is a one-piece surgical clamp assembly when shaft 71 resides within and slidably engages cylinder 80 without further assembly required, and when jaw members 75 and 76 open and close without any further assembly required.

The materials of construction of the surgical clamp can be any that are radiolucent. This would typify most plastics and, therefore, plastic is a preferable material of construction.

Referring again to FIGS. 5 and 6, a preferable embodiment of the present invention is shown with grooves 120 and 121. The grooves are respectively located on cooperating faces 125 and 126 of jaws 75 and 76. The presence of at least one is preferable and the presence of both is more preferable. The grooves are designed and adapted to compensate for the presence of a catheter inside a canal, vessel, duct, or body cavity when the clamp is simultaneously placed around the catheter and the tissue forming the passageway. The grooves minimizes damage caused by pinching the tissue residing between jaw members 75 and 76 and the catheter.

Figure 10:
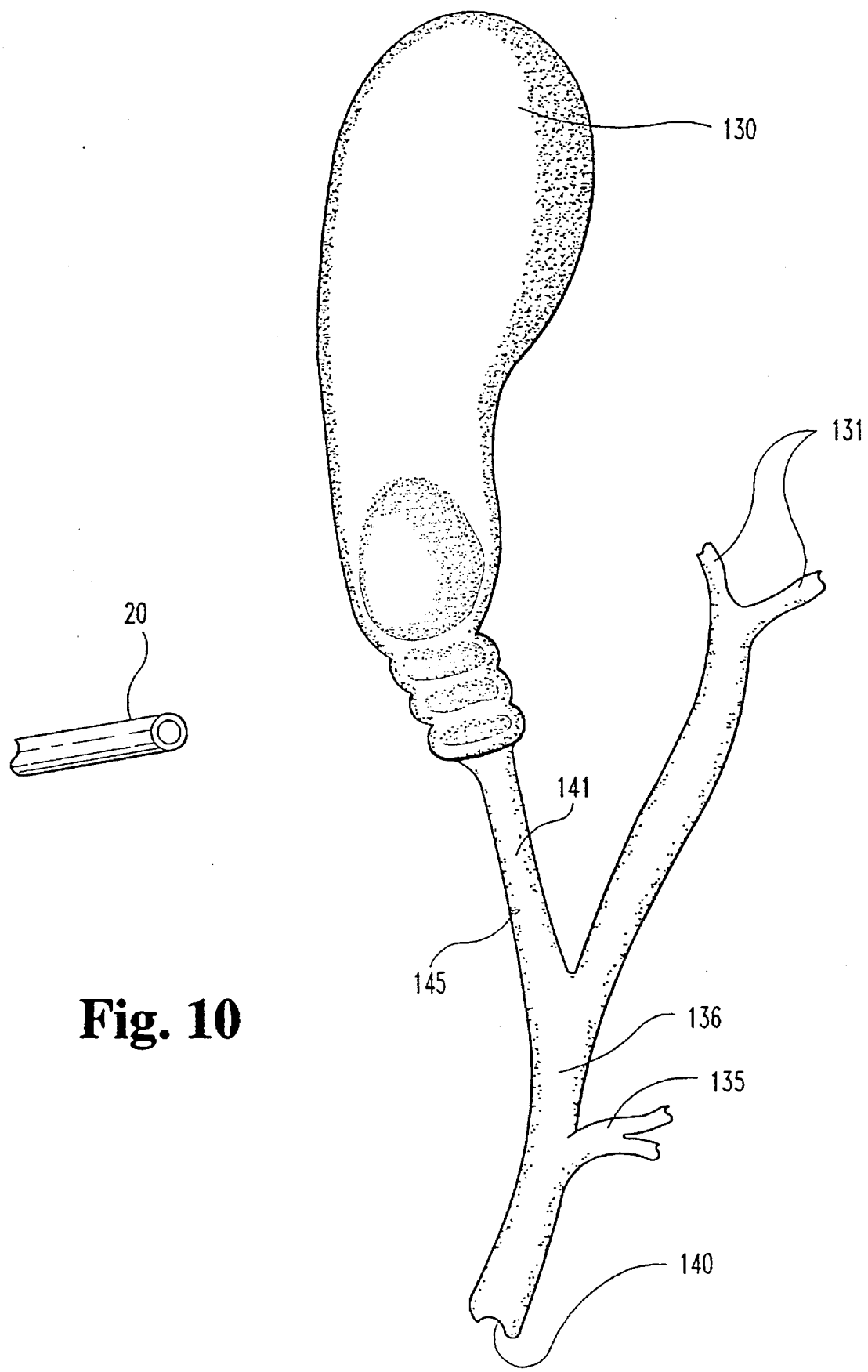
FIGS. 10 and 11 are plan views of a catheter assembly near a human gall-bladder according to one embodiment of the present invention.
Figure 11:
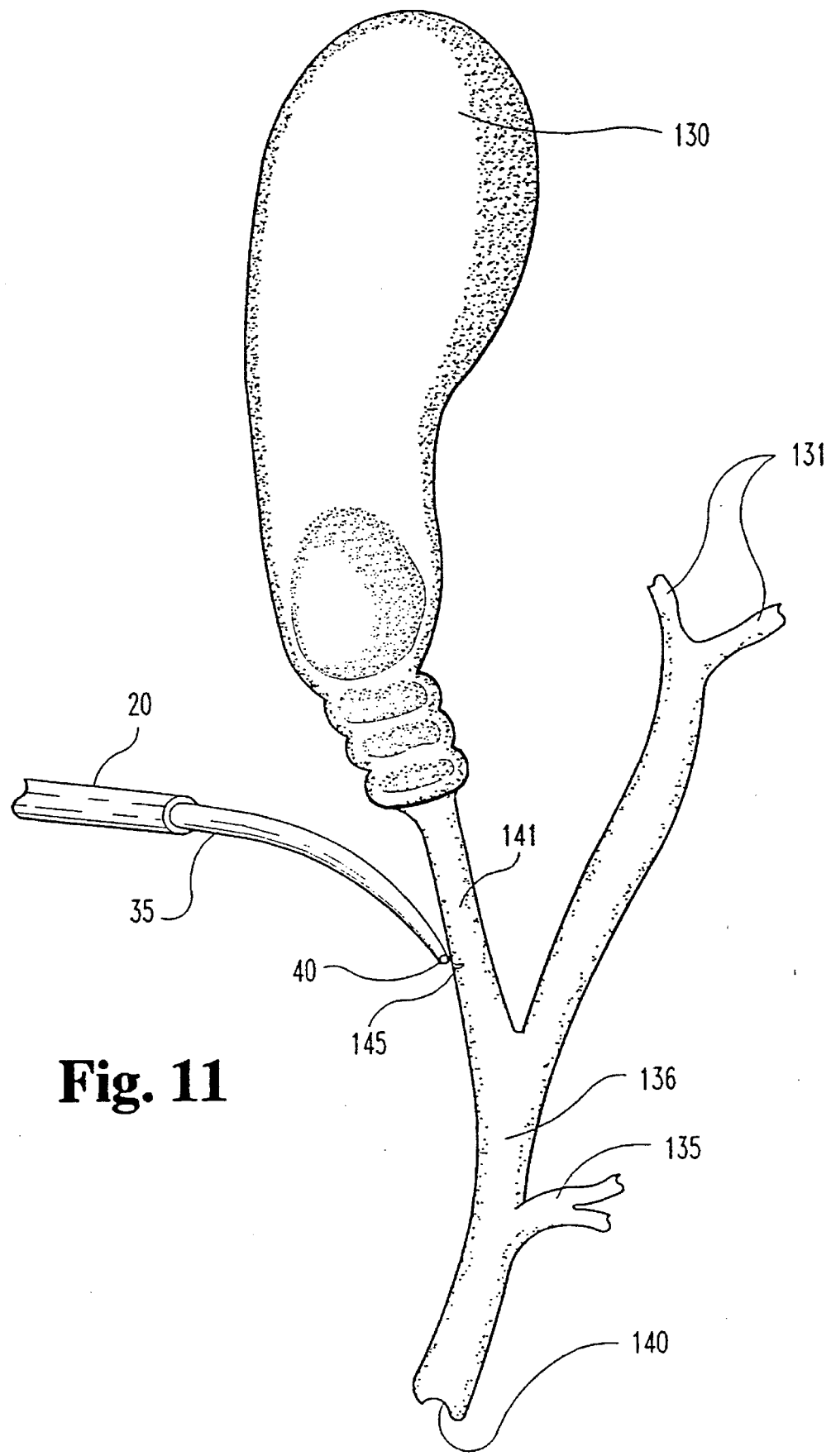

Referring now to FIGS. 10–14, there is shown a use of the present invention in a cholangiographic exam according to one embodiment of the present invention. FIGS. 10–11 show gall-bladder 130, hepatic ducts 131, pancreatic duct 135, common bile duct 136, entrance into the duodenum 140, and cystic duct 141.

Referring to FIG. 10, the three-piece catheter assembly contemplated by the present invention is inserted into the belly of the patient near gall bladder 130. The three-piece assembly including cannula 20, guide 35 slidably engaging and residing within cannula 20, catheter 50 slidably engaging and residing within guide 35, and catheter 50 and guide 35 being fully retracted within cannula 20.

Referring to FIG. 11, guide 35 is extended from cannula 20 and rotated as necessary to place distal end 40 of guide 35 to a position immediately adjacent transverse incision 145 in cystic duct 141.

Figure 12:
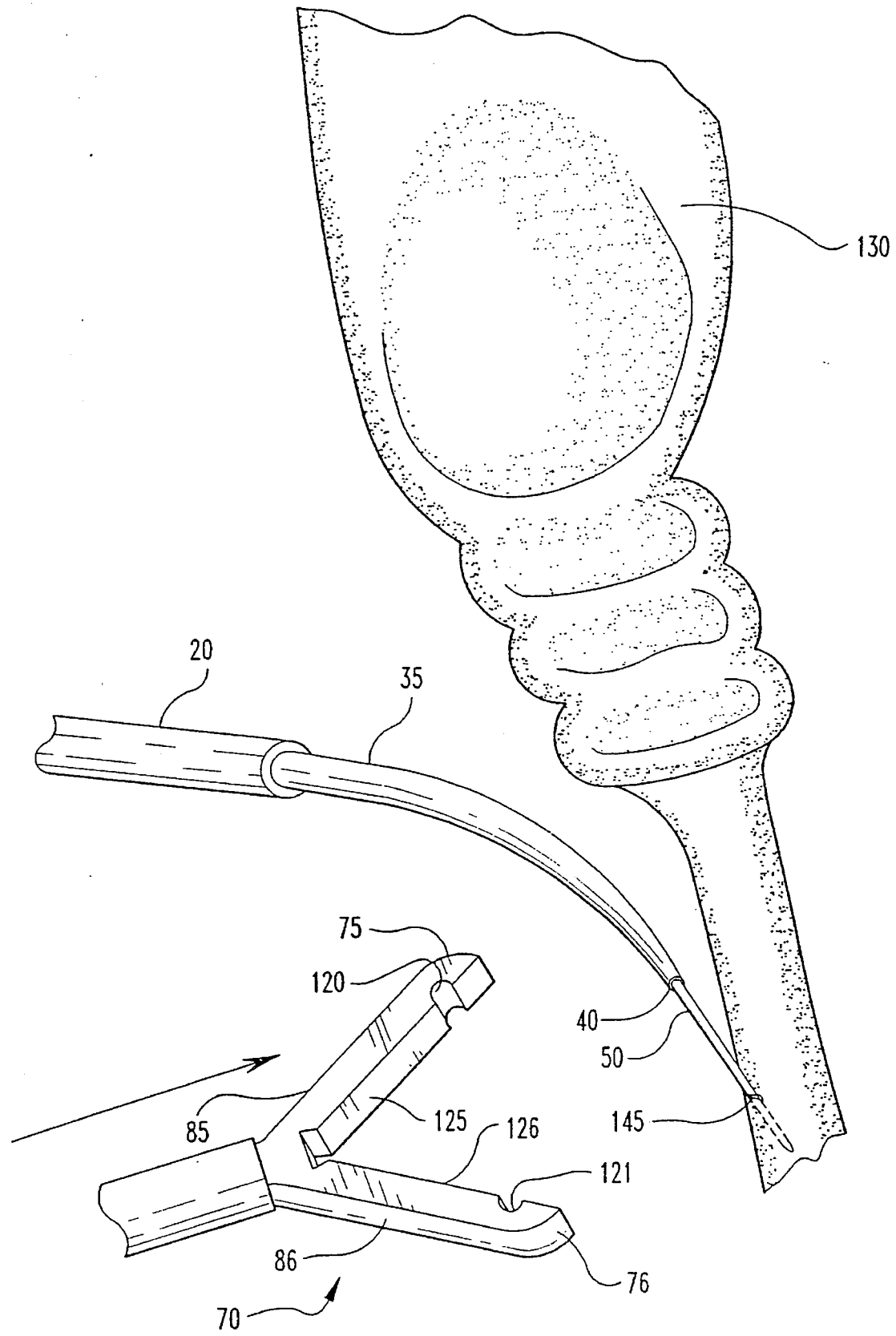
FIGS. 12 and 13 are plan views of a catheter assembly and surgical clamp near a human gall-bladder according to one embodiment of the present invention.

Referring to FIG. 12, catheter 50 is pushed past distal end 40, into incision 145, and into cystic duct 141. Surgical clamp 70 is then moved toward and eventually around cystic duct 141 to effect a seal. Jaws 75 and 76 are placed on each side of cystic duct 141 and cooperating faces 125 and 126 are pressed against the duct as jaws 75 and 76 are closed. Clamp 70 is to be positioned so that grooves 120 and 121 surround catheter 50.

Figure 13:
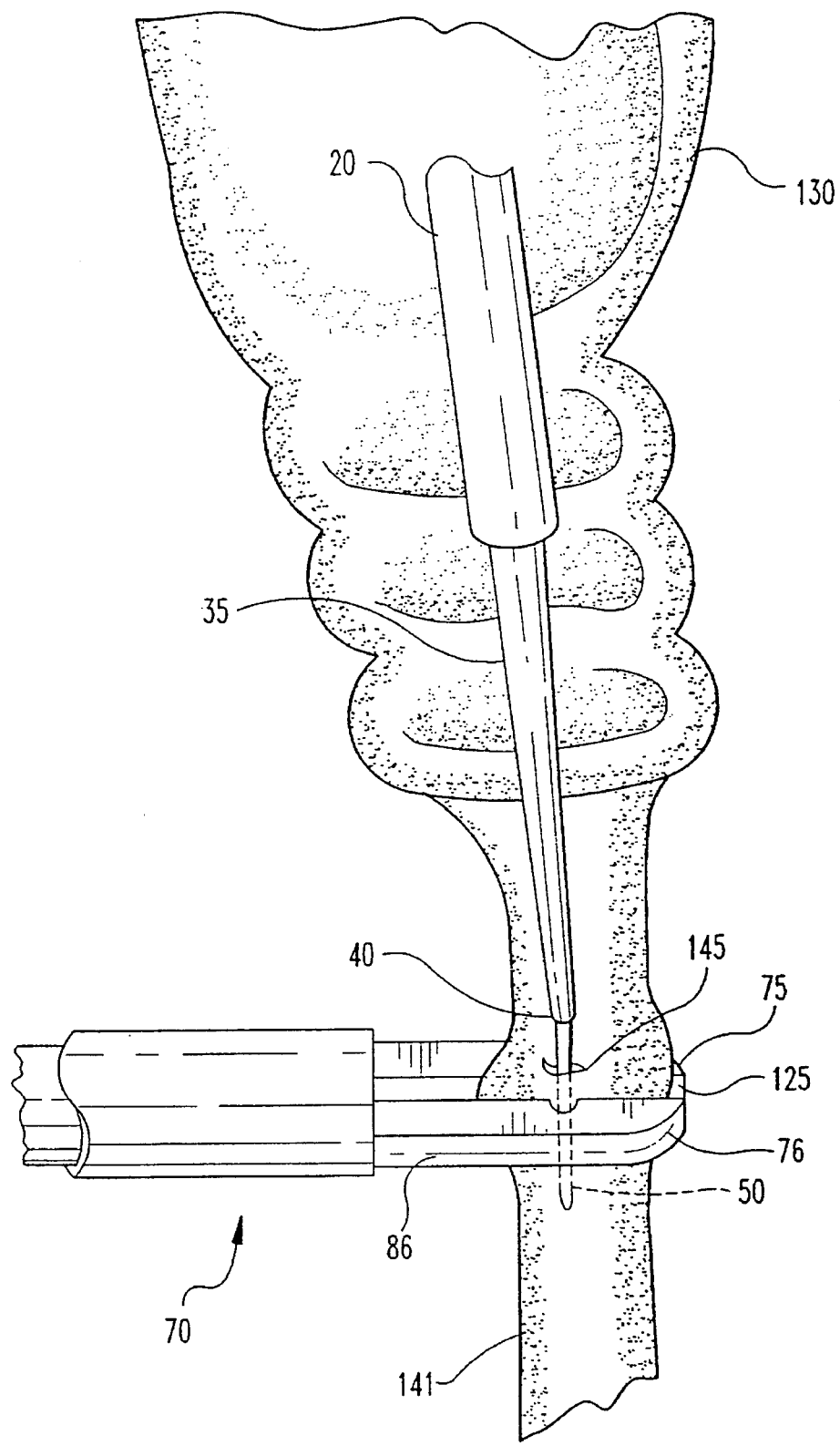

Referring to FIG. 13, surgical clamp 70 is shown in place around cystic duct 141 with grooves 120 and 121 postioned around catheter 50. The grooves help eliminate tissue damage to cystic duct 141 possibly caused by pinching the tissue between catheter 50 and jaws 75 and 76. The grooves also assist in effecting a tighter seal between the cystic duct and the gall-bladder. Irrigating saline solution and radiopaque dye are then alternately used as would normally occur during a standard cholangiographic exam.

A beneficial aspect of the present invention is that when a roentgenographic visualization is made, surgical clamp 70 and guide 35 do not block the the surgeons view. X-rays pass through the radiolucent material from which clamp 70 and guide 35 are formed. Therefore, they do not obstruct the view of tissue residing in line with these instruments and the X-ray source.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical clamp, comprising:

(a) a shaft with proximal and distal ends;

(b) two opposing jaw members with proximal ends, distal ends, cooperating faces, and lateral faces, said jaw members hingedly attached at their proximal ends to the distal end of said shaft, said jaw members adapted to clamp tissue placed between the cooperating faces;

(c) a cylinder slidably disposed around said shaft, said cylinder adapted to urge said opposing jaws together when said cylinder is axially displaced toward the distal end of said shaft and over the lateral faces of said jaw members; and (d) said shaft, said jaw members, and said cylinder formed of radiolucent material and wherein said cylinder has a longitudinal slot therein and said shaft is further comprised a finger positioner attached to the side of said shaft, said finger positioner extending from said shaft and through said cylinder at the longitudinal slot therein, said finger positioner adapted to convey force from a finger to axially displace said shaft within said cylinder.

2. The surgical clamp of claim 1, wherein two diametrically opposed finger positioners are attached to said shaft, said -two finger positioners extending from said shaft and through said cylinder at diametrically opposed longitudinal slots within said cylinder.

3. The surgical clamp of claim 1, wherein said shaft, said jaw members, and said cylinder are assembled so as to form a one-piece surgical clamp assembly.

4. A method for clamping surgical tissue, comprising:

(I) inserting a catheter inside a body portion selected from the group consisting of a canal, vessel, body cavity, and duct; and (II) simultaneously clamping the catheter and the body portion selected from the group consisting of a canal, vessel, body cavity, and duct with a surgical clamp including:
  (a) a shaft with proximal and distal ends;
  (b) two opposing jaw members with proximal ends, distal ends, cooperating faces, and lateral faces, said jaw members hingedly attached at their proximal ends to the distal end of said shaft, said jaw members adapted to clamp tissue placed between the cooperating faces;
  (c) a cylinder slidably disposed around said shaft, said cylinder adapted to urge said opposing jaws together when said cylinder is axially displaced toward the distal end of said shaft and over the lateral faces of said jaw members; and
  (d) said shaft, said jaw members, and said cylinder formed of radiolucent material; and
  (e) at least one of said cooperating faces has a groove therein which is simultaneously clamp around the body portion selected from the group consisting of a canal, vessel, body cavity, and duct and a catheter so as to minimize damage caused by pinching the tissue of the body portion residing between said jaw members and the catheter.

5. A method for clamping surgical tissue, comprising:

(I) inserting a catheter inside a body portion selected from the group of a canal, vessel, body cavity, and duct; and (II) simultaneously clamping the catheter and the body portion with a surgical clamp including:
  (a) a shaft with a shaft distal end portion;
  (b) two opposing jaw members with jaw proximal end portions, and cooperating faces, said jaw members movably attached at their jaw proximal end portions to the shaft distal end portion, said jaw members adapted to clamp tissue placed between the cooperating faces;
  (c) a cylinder slidably receiving said shaft, said cylinder adapted to urge said opposing jaws together when said cylinder is axially displaced toward the shaft distal end portion; and
  (d) said shaft, said jaw members, and said cylinder formed of radiolucent material; and
  (e) at least one of said cooperating faces has a groove therein which is simultaneously clamped around the body portion so as to minimize damage caused by pinching the tissue of the body portion residing between said jaw members and the catheter.

6. A surgical clamp, comprising:

(a) elongate first means with length;

(b) two opposing jaws with cooperating faces, said jaws movably attached to said elongate first means, said jaws adapted to clamp tissue placed between the cooperating faces;

(c) elongate second means slidably disposed relative to said elongate first means, said elongate second means adapted to urge said opposing jaws together when said elongate second means is axially displaced relative to said elongate first means toward said jaws; and (d) said elongate first means, said jaws, and said elongate second means formed of radiolucent material; and wherein;

said elongate second means has an opening therein and said elongate first means has a finger positioner attached to the side of said elongate first means, said finger positioner extending from said elongate first means and through said elongate second means at the opening, said finger positioner adapted to convey force from a finger to axially displace said elongate first means relative to said elongate second means.

7. The surgical clamp of claim 6 wherein two diametrically opposed finger positioners are attached to said elongate first means, said two finger positioners extending from said elongate first means and outwardly of said elongate second means.

* * * * *